(12) United States Patent
Lee

(10) Patent No.: US 8,788,010 B2
(45) Date of Patent: Jul. 22, 2014

(54) SENSOR FOR DETECTING BIOLOGICAL ELECTRO-MAGNETIC SIGNAL AND THE DIAGNOSTIC DEVICE USING THE SAME

(75) Inventor: Sang-Moon Lee, Seoul (KR)

(73) Assignee: Uni Bio-Tech., Inc., Seoul (KR)

( * ) Notice: Subject to any disclaimer, the term of this patent is extended or adjusted under 35 U.S.C. 154(b) by 725 days.

(21) Appl. No.: 12/278,772

(22) PCT Filed: Feb. 9, 2007

(86) PCT No.: PCT/KR2007/000734
§ 371 (c)(1),
(2), (4) Date: Aug. 22, 2008

(87) PCT Pub. No.: WO2007/091873
PCT Pub. Date: Aug. 16, 2007

(65) Prior Publication Data
US 2009/0182218 A1 Jul. 16, 2009

(30) Foreign Application Priority Data
Feb. 10, 2006 (KR) .................. 10-2006-0013170

(51) Int. Cl.
*A61B 5/00* (2006.01)
(52) U.S. Cl.
USPC ..................................................... 600/382

(58) Field of Classification Search
USPC .............. 600/372, 382, 395, 547; 324/248; 73/861.18; 340/518, 545.3, 551, 552
See application file for complete search history.

(56) References Cited

U.S. PATENT DOCUMENTS

| 5,039,981 | A | * | 8/1991 | Rodriguez | 340/551 |
| 5,646,526 | A | * | 7/1997 | Takeda et al. | 324/248 |
| 7,145,452 | B2 | * | 12/2006 | Jones | 340/518 |
| 7,754,245 | B2 | * | 7/2010 | Lee | 424/574 |

* cited by examiner

*Primary Examiner* — Max Hindenburg
(74) *Attorney, Agent, or Firm* — Joseph Hyosuk Kim; JHK Law

(57) ABSTRACT

The invention relates to a material for the detection of biological electro-magnetic signals made of a epidermis of a living organism and a diagnostic device using the same, and more particularly, to a material for the detection of biological electro-magnetic signals made of a epidermis of a living organism, through drying is one stage, also selecting is another stage of production, and a diagnostic device using the same. The material of the invention has an effect of detecting biological electro-magnetic signals. Accordingly, the material for the detection of biological electro-magnetic signals of the invention can be used for manufacturing a diagnostic device for detecting biological electro-magnetic signals non-invasively as well as effectively used in diagnosis in cases where biological electro-magnetic signals are changed by cancer, inflammations due to immunodeficiency and so on.

18 Claims, 8 Drawing Sheets

SENSOR FOR DETECTING BIOLOGICAL ELECTRO-MAGNETIC SIGNAL AND THE DIAGNOSTIC DEVICE USING THE SAME

TECHNICAL FIELD

The present invention relates to a material for the detection of biological electro-magnetic signals made of a epidermis of a living organism and a diagnostic device using the same, and more particularly, to a material for the detection of biological electro-magnetic signals made of a epidermis of a living organism, through drying and selecting, and a diagnostic device using the same.

BACKGROUND ART

All cells of a living body such as heart muscle, skeletal muscle, smooth muscle and nerve cell have electricity. Since such electricity can be changed by external stimulus or cell injury, the condition of a cell can be estimated by measuring the change. There are a number of electrical changes in the cell, ranging from a simple change which can be measured based on current variation through a single channel of a cell membrane to a combination of electrical behaviors of a number of cells. Such an electrical change inevitably accompanies a change of ions inside a cell such as Na+, K+ and CL− and a change in chemical elements such as amino acids, catecholamine and Peptide.

As well-known in the art, some diagnostic techniques such as electrocardiogram, magneto-cardiograph and magneto-encephalography are common methods to measure biopotential of a heart or brain of a living body in order to diagnose any disease of the living body. Accordingly, a number of approaches have been made to solve relevant clinical problems by understanding electrical and chemical stimulations of biological actions.

As an example, there have been approaches to diagnose a disease by measuring an electric resistance of an abnormal region (in particular, an inflamed region) of patients having various diseases ("*CHANGE IN ELECTRIC RESISTANCE OF THE SKIN OCCURRING IN THE RIGHT BELLY AT AN OUTBREAK OF ACUTE APPENDICITIS*", B. M. Vorochilov, Published by Eu-Hak (Medical Science), 1978, pp 46 to 49 and "*NUMERICAL EXPRESSION OF PAIN CAUSED BY RICULITIS OF THE SPINAL CORD, WHICH IS OBTAINED BY MEASURING ELECTRIC RESISTANCE OF THE SKIN*", B. M. Vorochilov, Published by Bu-Hak (Medical Science), 1982, pp 42 to 44). As another example, there has been an approach to measure the dielectric coefficient of cancer cells in view of the electric characteristics thereof ("*DIELECTRIC COEFFICIENT CHARACTERISTICS OF TUMOR TISSUE*", YU Don-Sik et al, published by Journal of Korea Electro-magnetic Engineering Society, 2002, Vol. 13, No. 16, pp 566 to 571.

In addition, there has been an approach to measure an abnormality in the body by using a magnetic field distribution around the body (LEE Yong-Ho et al., Korean Journal of Brain Science and Technology, 2002, Vol. 2, No. 2, pp 79 to 90). In particular, after the development of a highly sensitive magnetic flux meter using a Superconducting Quantum Interference Device (SQUID), it has been possible to measure a faint magnetic flux in the body. Accordingly, various studies are being actively carried out many countries to diagnose diseases by measuring a faint magnetic flux created from the viscera of the human body using the magnetic flux meter ("*BIOMAGNETIC FIELD DETECTION*," Kotani Makoto, Published by Corona Company, 1995).

That is, various attempts have been made continuously to diagnose diseases based on the fact that a different electric phenomenon between healthy and sick persons causes a different magnetic field distribution. For example, in order for a stomach to digest foods, stomach muscles should move while repeating contraction and relaxation. Such movements are controlled by electric signals flowing through the stomach muscles, transmitted through nerve cells. If such electric signals are abnormal, the stomach muscles may have a problem in their movement, which potentially causes an indigestion. The abnormal electric signals flowing through the stomach muscles show a different aspect from normal electric signals, thereby creating a different magnetic field distribution.

This symptom is true for not only indigestion but also other diseases such as cancer, disease by immunodeficiency and heart disease. It is possible to diagnose a disease from a subject by examining a change in an electro-magnetic field around a specific viscera or an electro-magnetic field pattern of a patient distinguished from that of normal persons. These schemes basically examine any changes in electro-magnetic signals in the human body or biological electro-magnetic signals.

However, such biological electro-magnetic signals or their changes are extreme precision the immensely subtle, minute signals to be used efficiently.

The epidermis of an animal refers to a type of epithelium that makes up the skin surface. The epidermis is mainly composed of a corneous substance, and conventionally has been regarded as mainly acting to protect the animal from external stimulation (Textbook Committee of Korean Dermatological Association, "*DERMATOLOGY*" (Revised version 4), pp 1-5, 2001).

When human epidermis is examined with respect to physiological characteristics or observed with an electron microscope and the like, a epidermis is of a matrix structure, including stratum nucleare composed of living cells and anucleate stratum corneum composed of dead horny substances without nucleii. Under the influence of electro-magnetic spectrum, a dielectric crystal changes optical properties and refractive constant, in which a change in polarization constant is proportional to an electro-magnetic field. Owing to the above-mentioned structure, the epidermis has a property of crystalline dielectric material.

The epidermis contains pigments such as melanin, which is created by melanin-creating cells melanoblast existing in an underlying layer of the epidermis and then converted into surrounding keratinocytes to represent skin color. Like the epidermis, the melanoblast originates from the neural crest differentiated from the ectoderm, and performs an important function of creating melanin to protect the skin from ultraviolet rays. The melanoblast having dendrites is morphologically similar with nerve cells, and commonly has a number of acceptors for growth factors and signal molecules. Thus it is appreciated that the melanoblast has the same morphological origin as the nerve cells (PARK Gyeon-Chan, "*Journal of the Society of Cosmetic Chemists of Korea*," Vol. 25, No. 2, p 45 내지 57, 1999). In addition, the above-mentioned observations are also supported by the fact that the epidermis differentiated from ectoderm has the same genetic origin as nerve cells such as brain, spinal cord and nerve.

According to studies on epidermis properties with respect to electro-magnetic signal creation and conduction, it was found that the epidermis not only protects the living body from external stimulation but also acts an independent function as a separate biological system in an organism ("*ELECTRICITY AND MAN*", V. E. Manoilov, 1988, pp 184 to 185).

In particular, it is also found that the epidermis shows various reactions such as reflection, absorption and dispersion to electro-magnetic waves incident into the epidermis.

Based on the above-mentioned facts, the inventors have analyzed physical, electrical, optical and photophysical properties of the epidermis and sought for available measures to utilize the epidermis. Through the studies, the inventors have found that the epidermis changes its electrical characteristics when an external electro-magnetic signal is applied thereto, functioning as a material detective to biological electro-magnetic signals. By using these symptoms, the invention has devised a material detective to biological electro-magnetic signals of the present invention.

DISCLOSURE OF THE INVENTION

Technical Problem

Therefore a first object of the present invention is to provide a material for the detection of biological electro-magnetic signals made of a epidermis of a living organism.

A second object of the invention is to provide a production method of a material for the detection of biological electro-magnetic signals from a epidermis of a living organism.

A third object of the invention is to provide a diagnostic device of a material for the detection of biological electro-magnetic signals made of a epidermis of a living organism.

Technical Solution

In order to realize the first object of the invention, the invention provides a material for the detection of biological electro-magnetic signals made of an epidermis of a living organism.

In order to realize the second object of the invention, the invention provides a production method of a material for the detection of biological electro-magnetic signals from an epidermis of a living organism.

In order to realize the third object of the invention, the invention provides a diagnostic device of a material for the detection of biological electro-magnetic signals made of a epidermis of a living organism.

Hereinafter the present invention will be described in detail.

The material for the detection of biological electro-magnetic signals of the invention is produced from a epidermis of a living organism, through drying and selecting.

Herein the term "epidermis" indicates skin or epidermal tissue of a living body, scale transformed from dermis, a retrogressed or cornified scale, a scale of a fish, a scale or horny scale layer of a reptile, a modified skin of a bird or mammal body, a cuticle of an insect, a cuticle of a mollusk, a cuticle of a shellfish, a scale including a cuticle of a vertebrate animal, a feather or hair, and a shell or horny scale layer of a crustacea. In these examples, cell tissue, extracellular tissue and so on are adhered pleomorphically, in a non-linear inharmony by connectives, forming a matrix. In addition, intracellular and extracellular, mainly, extracellular pigmentaton of, for example, melanin is observed.

The above-mentioned epidermis can be used without limitations for the production of a material of the invention. Preferably, the invention may use a scale of a fish, a scale or skin of a reptile, a cuticle of an insect and a shell of a crustacea. More preferably, the invention may use a scale of a crucian carp, a scale of a carp, a scale of a salmon, a scale of a trout, a scale of a turtle, a scale of a snapping turtle, a scale of a crocodile, a scale(skin) of a snake, a cuticle of a beetle, a cuticle of a grasshopper, a cuticle of a gold bug, a cuticle of a ladybug, a shell of a crab, a shell of a shrimp and a shell of a crayfish.

The epidermis may be preferably separated from a dead body. While the separation step is not limited to a specific procedure, it is preferable to separate the epidermis after being immersed in water such as distilled water or tap water at a temperature of 0° C. to 35° C. for 1 day to 30 days. The immersion can uniformly hydrate the epidermis, thereby reducing potential injury to the epidermis in the separation. Then, the immersed epidermis may be preferably separated from the dead body by physical force.

A drying step is aimed to stabilize electrical properties of the epidermis without having to damage a matrix structure of the epidermis. While the drying step is not specifically limited, it is preferable to dry the epidermis in a place of good ventilation which is out of the sunlight. The epidermis may be injured if it is dried rapidly by an artificial method using a heater and the like. The epidermis is then spread flat, optionally, between paper or cloth sheets so as not to be folded, and dried in the shade out of the sunlight under a pressure of 0.5 $kg/cm^2$ to 10 $kg/cm^2$ at room temperature (25° C.) for 1 hour to 48 hours. Then, the epidermis is dried in the shade without pressure at room temperature until moisture is completely removed. The drying time is not specifically limited, but is preferably 1 hour to 96 hours, and more preferably 24 to 48 hours.

If the epidermis is not sufficiently dried, remaining moisture reduces conductivity, permittivity and capacitance. Such reduced properties may lead to a variation in capacitance value, thereby degrading overall reliability of the material.

After the above drying step, the epidermis is selected. The selecting step includes cutting the dried epidermis into circles having a diameter of 0.1 to 10 mm, measuring the capacitance of the epidermis, and selecting the epidermis having a capacitance range from 0.1 pF to 100 pF. The selected epidermis is used as a sensor, stacked one or lap over 10 sensors. Here, the term "stacked or stacking" means tightly attaching and bonding a plurality of epidermis in a direction perpendicular to the epidermis plane so that the epidermis can be used as one unit. In particular, as the ability of the material of the invention to detect biological electro-magnetic signals can be more efficiently realized by using a single epidermis at a thickness of 0.01 mm to 10 mm or stacking 2 to 10 epidermis one on another in a case where the epidermis has a matrix layer and a melanin crystalline structure formed in an excellent state, it is preferable to previously select those epidermis that has an excellent matrix layer and melanin crystalline structure with a thickness corresponding to the above-mentioned range. In particular, a stack of 2 to 10 epidermis is preferable since biological electro-magnetic signals can be detected more easily.

In addition, the method of producing the material for the detection of biological electro-magnetic signals of the invention further includes a step of immersing the epidermis of a living body into water such as distilled water and tap water. The immersing step is carried out according to the above-mentioned procedures.

Furthermore, the method of producing the material for the detection of biological electro-magnetic signals of the invention further includes a step of measuring the conductivity of the epidermis and selecting the epidermis. Here, the conductivity is preferably in the range from 0.01 nS to 20 nS.

Moreover, the method of producing the material for the detection of biological electro-magnetic signals of the invention further includes a step of measuring the permittivity of the epidermis and selecting the epidermis. Here, the permittivity is calculated according to an equation of $\in = c \cdot d/\in_0(A$, where $\in$ indicates permittivity, c indicates conductivity, d indicates the thickness of the material for the detection of biological electro-magnetic signals, $\in_0$ is $8.85 \times 10^{-12}$ F/m, and A indicates the electrode area). Preferably, the permittivity ranges from 0.1 F/m to 50 F/m.

The biological electro-magnetic signal detective material produced by the above-mentioned method can be used as a sensor to detect electro-magnetic signals, in particular, biological electro-magnetic signals.

By using the material for the detection of biological electro-magnetic signals of the invention produced as above, a diagnostic device (sensor) can be manufactured. The diagnostic device includes a sensor probe having a material for the detection of biological electro-magnetic signals as defined above and electrodes in contact with both ends of the material for the detection of biological electro-magnetic signals in a thickness direction of the material for the detection of biological electro-magnetic signals; an analog circuit functioning to generate and adjust a frequency, the analog circuit connected to the sensor probe and having an frequency oscillation tuning circuit and a frequency allocator; and a digital conversion circuit connected to the analog circuit, the digital conversion circuit functioning to analyze and display a frequency signal and having an output part including one of a CPU, LCD and communication module and a storage part.

The sensor probe of the diagnostic device has the material for the detection of biological electro-magnetic signals and the electrodes contacting both ends of the material for the detection of biological electro-magnetic signals. The material for the detection of biological electro-magnetic signals is produced by the above-mentioned producing method. The electrodes serve to electrically connect the material for the detection of biological electro-magnetic signals to the circuit of the diagnostic device, and contact the material for the detection of biological electro-magnetic signals in a thickness direction of the material for the detection of biological electro-magnetic signals. The electrodes can be made preferably of Ag or Cu.

The analog circuit has the frequency oscillation tuning circuit and the frequency allocator, and is connected to the sensor probe. The frequency oscillation tuning circuit includes a frequency generator for generating a specific reference frequency, a frequency controller for controlling the reference frequency received through the sensor probe and a frequency amplifier for amplifying the reference frequency. The frequency allocator acts to allocate the frequency so as to be processed by the digital conversion circuit.

The digital conversion circuit includes the CPU for measuring the reference frequency and processing various operations, the output part for displaying the result processed by the CPU and the storage part for storing the result. The output part can be implemented with a common LCD window or a common communication module, and the storage part can be implemented with a common RAM and/or ROM.

The diagnostic device of the invention may further include a power circuit for supplying power to the analog circuit and the digital conversion circuit. The power circuit has a battery and a regulator for regulating a voltage necessary for the analog circuit and the digital conversion circuit, and may further have a common battery charging circuit.

Biological electro-magnetic signals can be measured by contacting the diagnostic device to a region to be measured and then operating the diagnostic device. The measurements are carried out non-invasively, and thus do not cause any side effects such as injection and radiation exposure. Information obtained from the measurement result can be analyzed to diagnose various diseases accompanied with cancer or inflammation.

According to an embodiment of the invention, the material for the detection of biological electro-magnetic signals is produced by drying and selecting the epidermis.

According to another embodiment of the invention, the diagnostic device is manufactured using the material for the detection of biological electro-magnetic signals.

Advantageous Effects

As set forth above, the material of the invention has an effect of detecting biological electro-magnetic signals. Accordingly, the material for the detection of biological electro-magnetic signals of the invention can be used for manufacturing a diagnostic device for detecting biological electro-magnetic signals non-invasively as well as effectively used in diagnosis in cases where biological electro-magnetic signals are changed by cancer, inflammations due to immunodeficiency and so on.

BRIEF DESCRIPTION OF THE DRAWINGS

FIG. 10 is a graph illustrating that a subject is diagnosed to be in a normal state by the diagnostic device;

FIG. 11 is a graph illustrating that a subject is diagnosed to be in a normal state by the diagnostic device;

FIG. 12 is a graph illustrating that a subject is diagnosed to be in a inflammation state by the diagnostic device;

MAJOR REFERENCE SIGNS OF THE DRAWINGS

Figure 1:
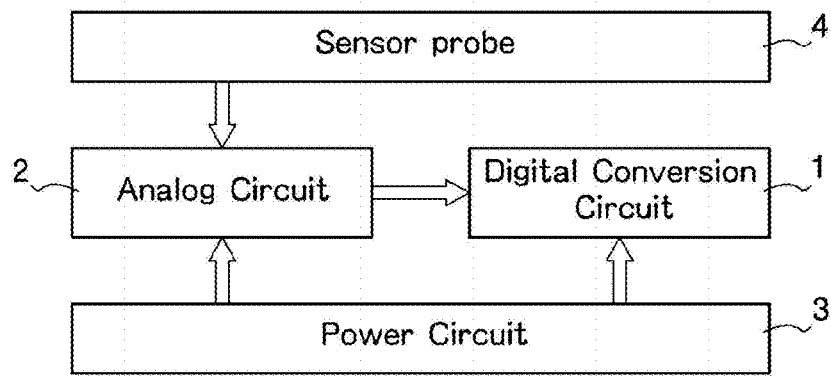
FIG. 1 is a block diagram illustrating an exemplary diagnostic device equipped with a material for the detection of biological electro-magnetic signals according to the invention.

1: digital conversion circuit
2: analog circuit
3: power circuit
4: sensor probe
11: CPU 12: flash memory
12a: ROM selector
12b, 12c: ROM
13: SDRAM
14: LCD inverter
15: LCD
16: PWM module
16a: frequency control oscillator
16b: buzzer
17: frequency input unit
18: channel selection unit
19: communication module
19a: radio communication module
19b: USB port
19c: RS-232C
20: frequency oscillation tuning circuit
21: low pass filter
22: 8 channel multiplexer
23: sensor selection unit
24: frequency controller
25: frequency generator
26: frequency signal amplifier
27: frequency allocator
31: adaptor
32: battery charge measurement circuit
33: battery charging circuit
34: battery
35: 3.3 volt regulator
36: 2.5 volt regulator
37: 5 volt regulator

BEST MODE FOR CARRYING OUT THE INVENTION

Figure 2:
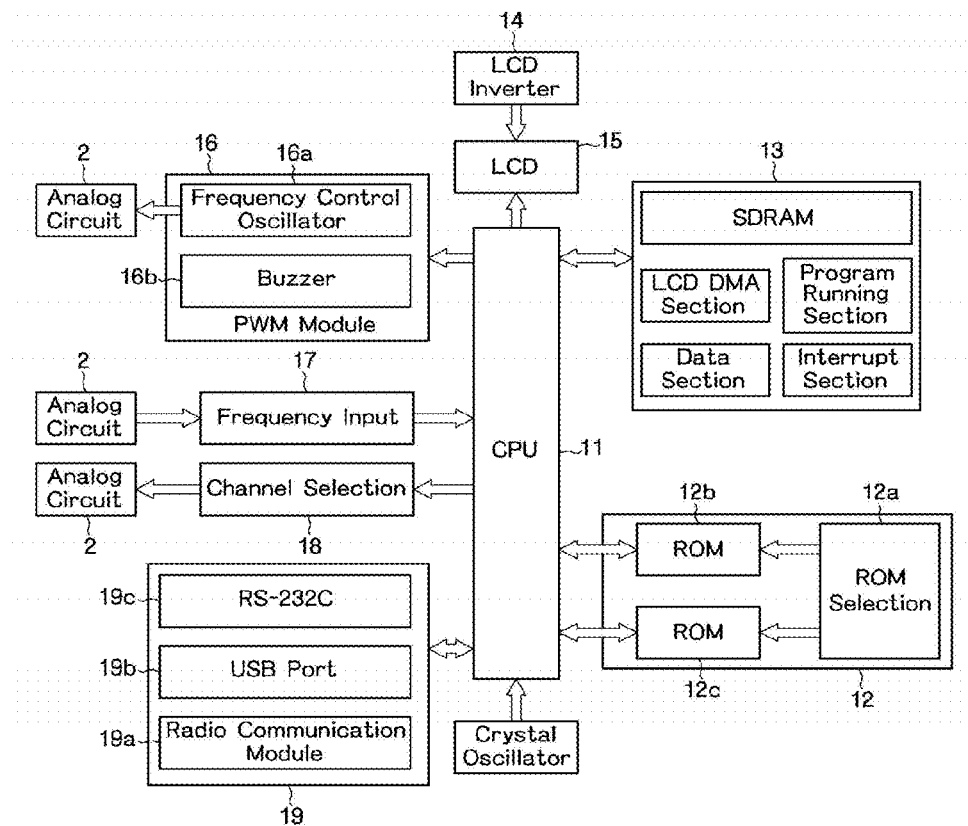
FIG. 2 is a block diagram illustrating a digital conversion circuit of the diagnostic device of the invention.
Figure 3:
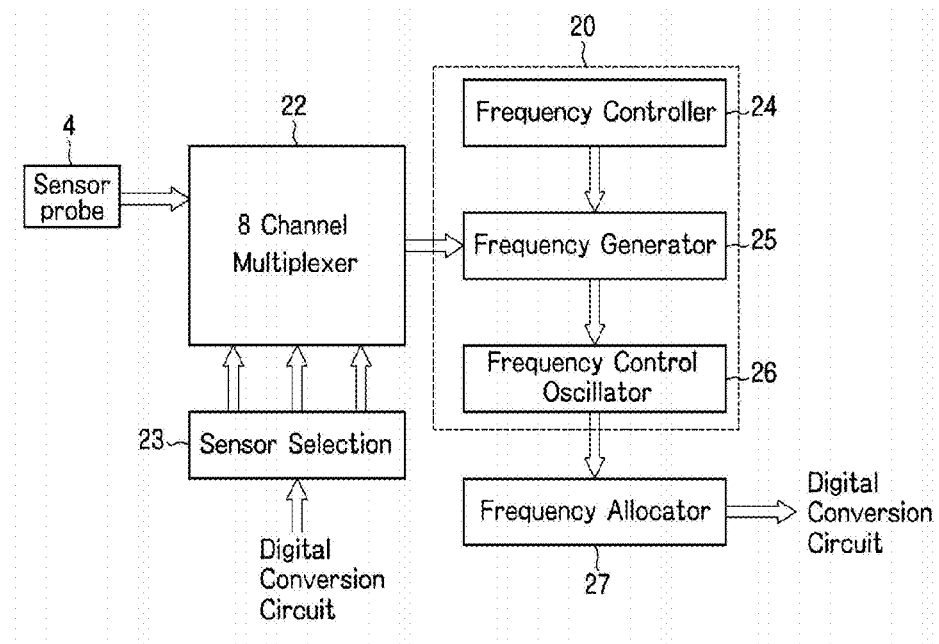
FIG. 3 is a block diagram illustrating a sensor probe and an analog circuit of the diagnostic device of the invention.

FIG. 1 is a block diagram illustrating an exemplary diagnostic device according to the invention. Referring to FIG. 1, the diagnostic device includes a digital conversion circuit (1), an analog circuit (2), a power circuit (3) and a sensor driver or sensor probe (4). As shown in FIG. 2, the digital conversion circuit (1) includes a CPU (11), flash memory (12), an SDRAM (13), an LCD (15), an LCD inverter (14) for adjusting the brightness of the LCD (15), a PWM module (16), a frequency input unit (17), a channel selection unit (18) and a communication module (19) for communicating with an external device. Referring to FIG. 3, the analog circuit (2) includes an 8-channel multiplexer (22), a sensor selection unit (23), a frequency controller (24), a frequency generator (25), a frequency signal amplifier (26) and a frequency allocator (27). The power circuit (3) includes an adaptor (31), a battery (34), a battery charging circuit (33), a battery charge measurement circuit (32), a 3.3-volt regulator (35), a 2.5-volt regulator (36) and a 5-volt regulator (37).

Figure 6:
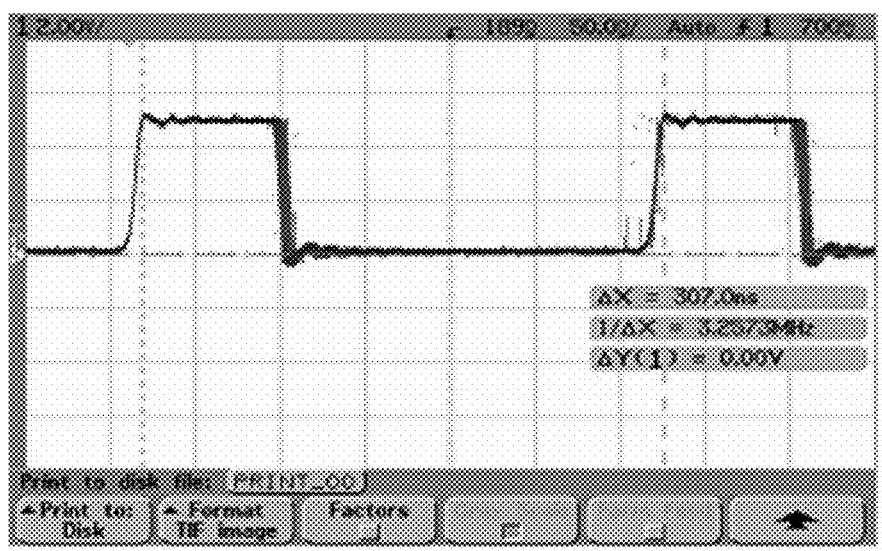
FIG. 6 is a graph illustrating a waveform of a frequency generated from the frequency generator of the analog circuit.

Describing the operation of respective parts, the frequency generator (25) of the analog circuit (2) generates a reference frequency. The reference frequency is unique to a material for the detection of biological electro-magnetic signals as shown in FIG. 6, based on a capacitance component of the material for the detection of biological electro-magnetic signals of the sensor probe (4) prior to diagnosis. The reference frequency prior to diagnosis is controlled by the frequency controller (24) so that the frequency generator (25) can generate a more precise reference frequency. In particular, the frequency controller (24) minimizes errors such as an error occurring in a case where the material for the detection of biological electro-magnetic signals of the sensor probe (4) is multi-channeled, a basic fabrication error of electronic parts and an environmental error of a measuring position in order to control the frequency of a frequency oscillation tuning circuit (20) by the reference frequency of the material for the detection of biological electro-magnetic signals.

The material for the detection of biological electro-magnetic signals of the sensor probe (4) can be fabricated with various channels from single to multiple channels. In the case of multiple channels, the 8 channel multiplexer (22) and the sensor selection unit (23) are required.

Since the frequency signal generated from the frequency generator (25) is too extreme precision the immensely subtle, minute signals to be inputted directly into the digital conversion circuit (1), the frequency signal amplifier (26) amplifies the extreme precision the immensely subtle, minute signals up to a level that can be used in the digital conversion circuit (1). The signal amplified by the frequency amplifier (26) is a rapid frequency on the order of several MHz, which is then allocated by the frequency allocator (27) so that it can be measured in the digital conversion circuit (1).

The frequency signal process as above is inputted into the frequency input unit (17) and the channel selection unit (18). The frequency signal inputted into the CPU (11) by the frequency input unit (17) is calculated as a frequency value by the CPU (11).

In the case of manufacturing the material for the detection of biological electro-magnetic signals of the sensor probe (4) according to the invention, the basic capacitance of the material for the detection of biological electro-magnetic signals is varied slightly according to processes of manufacturing the material for the detection of biological electro-magnetic signals of the sensor probe (4). Therefore, when the reference frequency is adjusted in the analog circuit (2) as shown in FIG. 6, the reference frequency value can be varied slightly for each channel owing to a change in the capacitance.

Figure 7:
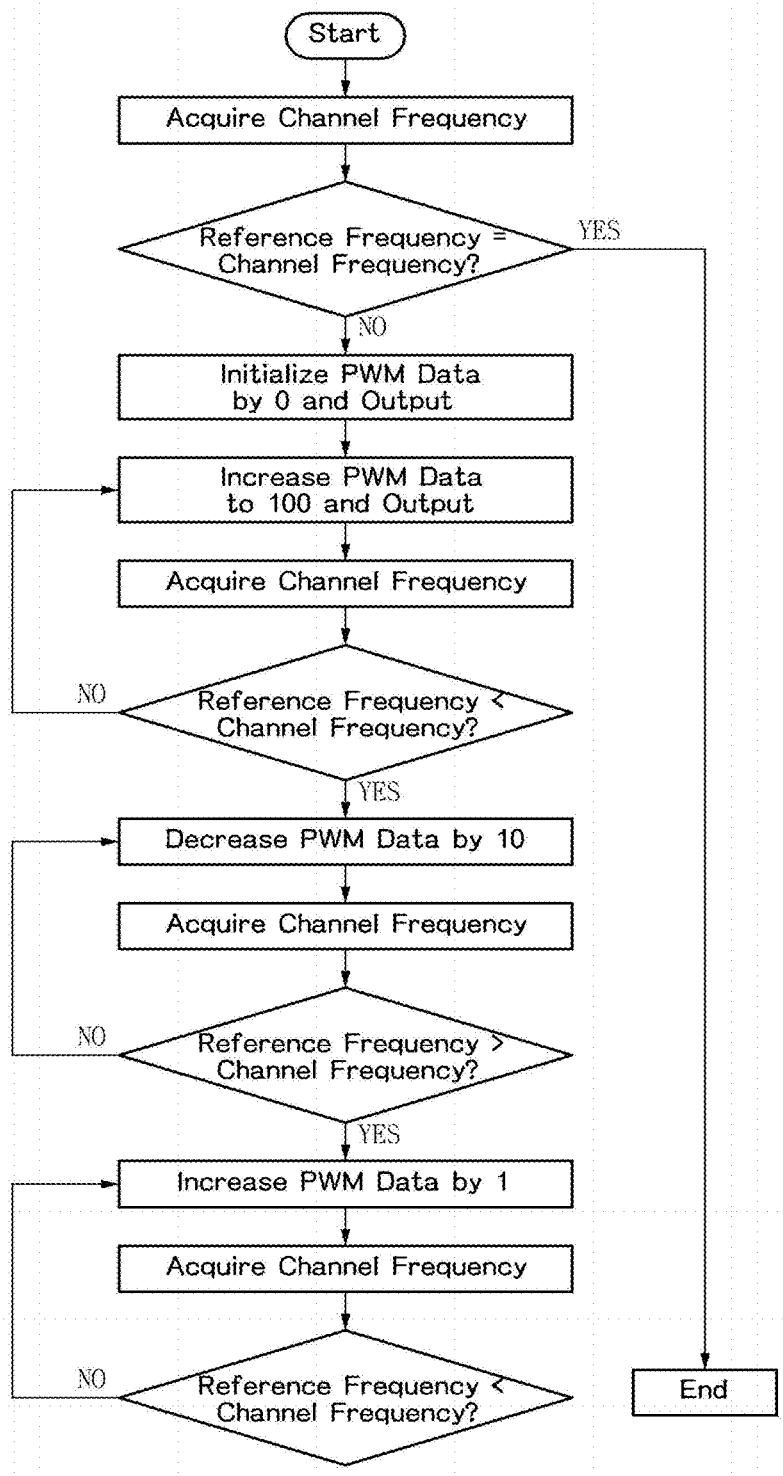
FIG. 7 is a flowchart illustrating a process of setting a channel frequency by the frequency controller.

Therefore, a process of reference frequency control is carried out according to an algorithm shown in FIG. 7. That is, channels are selected by the frequency selection unit (18), the reference frequency of a material for the detection of biological electro-magnetic signals for each channel is set by using the frequency control oscillator (16a), and then the CPU (11) stores sequentially channel values in memory areas of the SDRAM (13). Then, whenever frequencies are read from channel data of the material for the detection of biological electro-magnetic signals, the stored data is outputted by the frequency control oscillator (16a) and the operation is repeated.

In measurement, an electro-magnetic signal is inputted into the material for the detection of biological electro-magnetic signals, changing the capacitance of the material for the detection of biological electro-magnetic signals in each channel of the sensor probe (4). Then, a frequency change takes place in a reference frequency as shown in FIG. 6. The CPU calculates a frequency value, and allocates an area in the flash memory (12) to store the measured frequency. The difference between the reference frequency and the measured frequency is referred to as delta frequency, which can be calculated and stored in the allocated area in the flash memory (12) by the CPU (11).

Preferably, the CPU (11) controls the operation of the frequency control oscillator (16a) to adjust the frequency applied to the buzzer (16b) so that the buzzer (16b) can generate different sounds according to frequencies or delta frequencies. Alternatively, the CPU (11) may be adapted to display different colors on a display unit according to frequencies or delta frequencies. That is, one of green, yellow and red can be displayed selectively. Thus, in the diagnostic device of the invention, the LCD (15) selectively outputs green, yellow and red as the CPU (11) makes a determination according to frequencies or delta frequencies.

When the diagnostic device is powered on and actuated, a reference frequency is established. As a diagnosis begins, a frequency a measured according to the health condition of a subject, and a difference between the reference frequency and the measured frequency is calculated as a delta frequency. The health condition of the subject can be judged based on the magnitude of the measured frequency or delta frequency. Furthermore, since the magnitude of the measured frequency or delta frequency is a value proportional to a change in the capacitance of the material of the invention, the health condition of the subject can be judged based on the change in the capacitance of the material.

The CPU (11) is linked with the communication module (19) composed of a radio communication module (19a), a USB port (19b), an RS-232C (19c) and so on, and thus can transmit a frequency or delta frequency to an external device such as a PC. Data is transmitted to an external processing device via various communication modes, and can be displayed, stored, outputted and processed into a database.

An operation by the analog circuit (2) to process a frequency signal will now be described.

First, biological electro-magnetic signals of a subject such as a human body, which is detected by (being inputted into) the material for the detection of biological electro-magnetic signals of the sensor probe (4), causes a change in the capacitance of the material. To measure a variation in the capacitance, the capacitance is converted into a frequency by the frequency oscillation tuning circuit (20). The frequency oscillation tuning circuit (20) includes the frequency controller (24), the frequency generator (25) and the frequency signal amplifier (26) as shown in FIG. 3. The frequency oscillation tuning circuit (20) causes an oscillation to the reference frequency, as shown in FIG. 6, which is unique to and based on the material for the detection of biological electro-magnetic signals of the sensor probe (4).

When biological electro-magnetic signals of a subject are detected by (being inputted into) the material for the detection of biological electro-magnetic signals of the sensor probe (4), the capacitance of the material change increases. The increased capacitance of the material decreases the frequency inputted into the digital conversion circuit 1 from the analog circuit (2), generated by the frequency oscillation tuning circuit (20). The oscillated frequency has a minute amplitude, and thus the frequency signal amplifier (26) amplifies the frequency to a predetermined level so that the digital conversion circuit (1) can measure the frequency.

Since the material for the detection of biological electro-magnetic signals of the sensor probe (4) may be used variously from a single channel to multiple channels, the 8-channel multiplexer (22) and the sensor selection unit (23) are used to measure all channels.

The signal transmitted from the analog circuit (2) to the digital conversion circuit (1), that is, the frequency oscillated by the frequency oscillation tuning circuit (20) is divided by the frequency allocator (27) so as to be easily measured by the digital conversion circuit (1).

An operation by the digital conversion unit (1) to process a frequency signal will now be described.

The digital conversion circuit (1), as shown in FIG. 2, includes the flash memory (12) for storing measured data and program data, an SDRAM (13) used as a temporary memory, the CPU (11) for measuring frequencies and processing various operations, the switch circuit (not shown) for receiving commands from a user, the PWM module (16) having a buzzer (16b) for generating sounds according to input frequencies, the LCD (15) and LCD inverter (14) for displaying calculated measurement data on a Graphic User Interface (GUI) and a communication module (19) for communicating with a PC and the like.

The digital conversion circuit (1) needs a frequency measurement algorithm for measuring frequencies outputted from the analog circuit (2). To measure the frequencies, the clock of the CPU (11) is counted for one period of the clock signal of the reference frequency of the material for the detection of biological electro-magnetic signals shown in FIG. 6, inputted through an input/output module of the CPU (11). The frequencies (F) are measured according to following Formula:

$$F=1/T$$

$$T=(\text{CPU Clock Counter})\times 1/(\text{CPU Frequency})$$

Prior to diagnostic measurement, the reference frequency is oscillated by the frequency oscillation tuning circuit (20), based on the capacitance of the material for the detection of biological electro-magnetic signals of the sensor probe (4). Biological electro-magnetic signal detected by (being inputted into) the material for the detection of biological electro-magnetic signals of the sensor probe (4) increase the capacitance of the material, which decreases the measurement frequency. Then, the decreased frequency is subtracted from the reference frequency to obtain a delta frequency.

Clinically speaking, the delta frequency indicates the amount of biological electro-magnetic signals. Accordingly, an increase in the delta frequency indicates a large amount of biological electro-magnetic signals, whereas a decrease in the delta frequency indicates a small amount of biological electro-magnetic signals.

The inventors made the diagnostic device of the invention display delta frequencies in three stages. The first stage indicates a normal behavior in the biological electro-magnetic signals, the second stage indicates an active behavior in the biological electro-magnetic signals and the third stage indicates a pulsatory behavior in the biological electro-magnetic signals.

Figure 5:
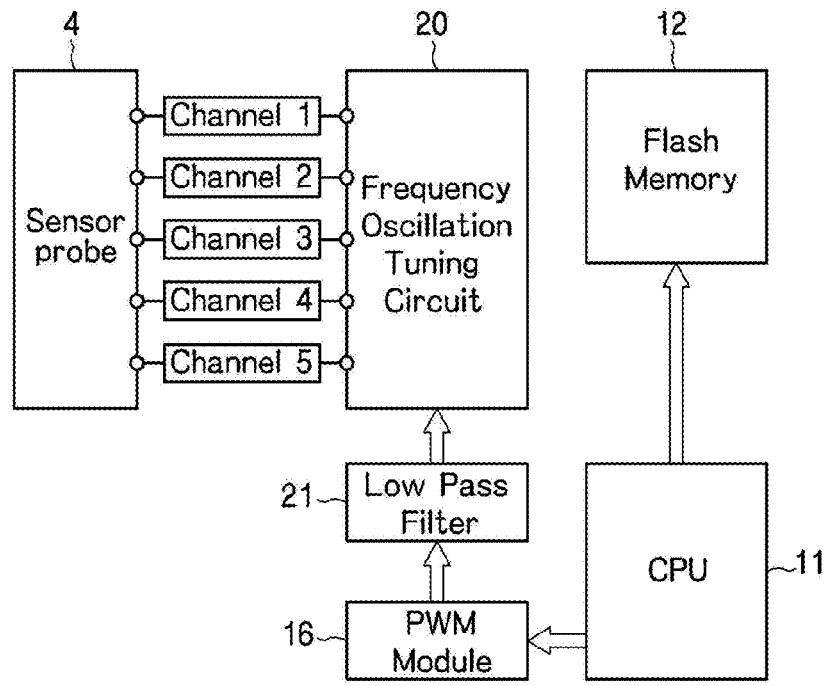
FIG. 5 is a block diagram illustrating a frequency oscillation tuning circuit along with surrounding circuits.

Even though the reference frequency based on the non-diagnosed state is controlled by the frequency controller (24), the reference frequency may not be maintained correctly but has a minute difference in a process of calculating the frequency in the digital conversion circuit (1). The frequency control oscillator (16a) is also provided in the digital conversion circuit (1) to cope with such a symptom as well as control the frequency precisely. As shown in FIG. 5, a frequency setting unit includes the sensor probe (4) having a material for the detection of biological electro-magnetic signals, the frequency oscillation tuning circuit (20), the low pass filter (21), the CPU (11) having input and output ports, the PWM module (16), the flash memory (12) and the like.

As the CPU (11) is powered on, it receives a frequency from the analog circuit (2) and compares the received frequency with a reference frequency. If the received frequency is different from the reference frequency, it is controlled by the CPU (11).

Figures 10, 11, 12:
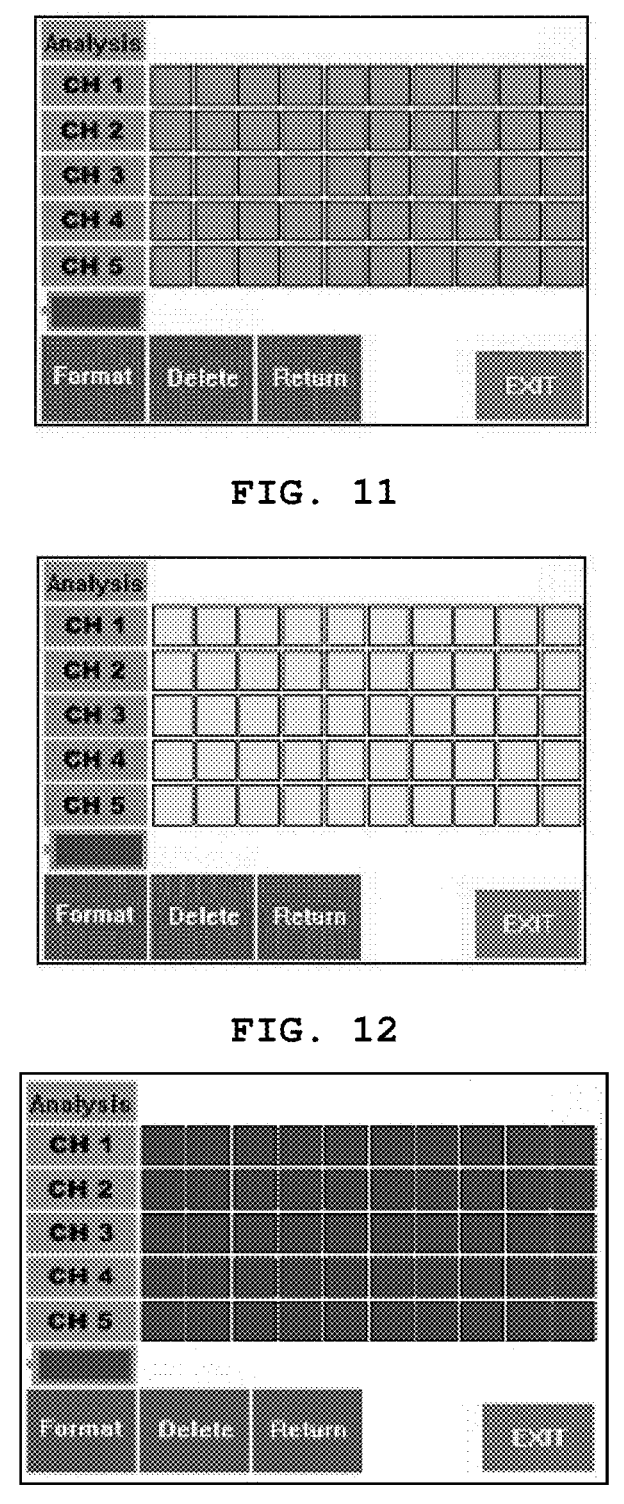
Figure 13:
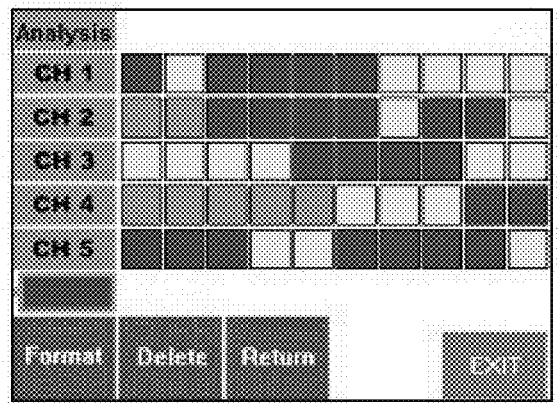
FIG. 13 is a graph illustrating that a subject is diagnosed with cancer by the diagnostic device.

When biological electro-magnetic signals from a subject or a living body is measured by the diagnostic device including the material for the detection of biological electro-magnetic signals of the invention, "green" or "yellow" indicators are shown uniformly as shown in FIGS. 10 and 11 in the case that the health condition of subjective mouse is very normal or normal. However, in the case of inflammation, a "red" indicator is shown uniformly as shown in FIG. 12. In the case of cancer, "red" and "yellow" indicators are shown irregularly as shown in FIG. 13.

Figure 8:
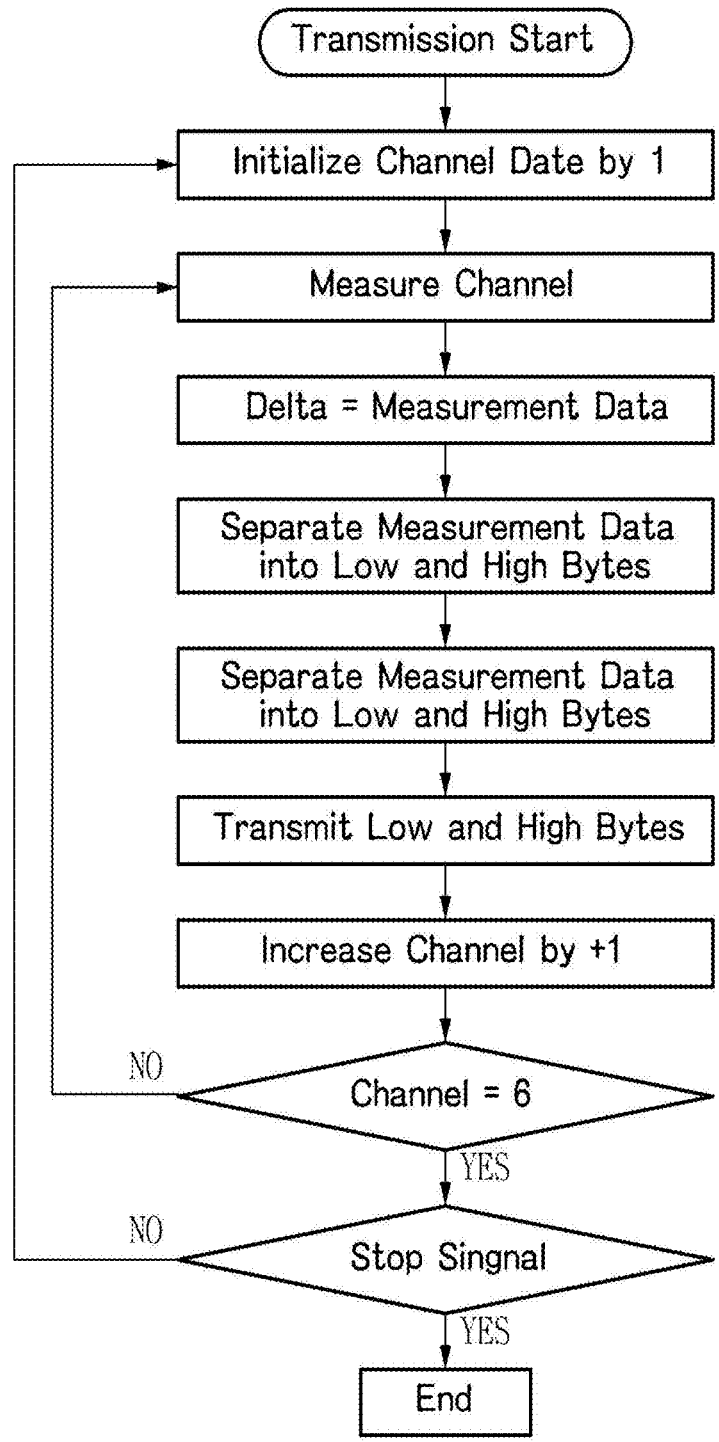
FIG. 8 is a flowchart illustrating a measuring process in a prescan mode of the diagnostic device.
Figure 9:
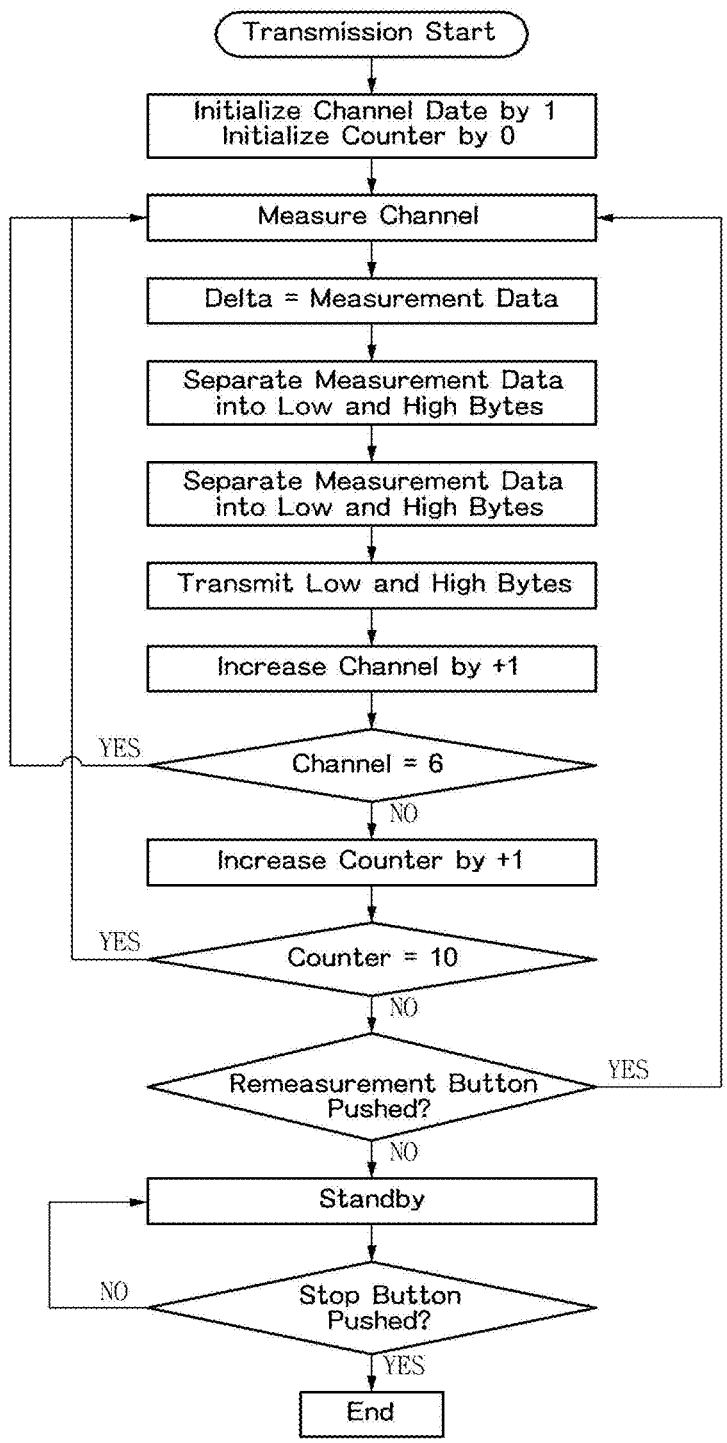
FIG. 9 is a flowchart illustrating a measuring process in a precise mode of the diagnostic device.

In this case, the degree of irregularity or variation of delta frequency is different according to human subjects or cancer status. In order to measure it more precisely, frequency sampling rate is classified into three types. FIG. 8 illustrates a channel draw mode which reads material frequencies at 10 ms and a prescan mode which reads material frequencies at 20 ms, and FIG. 9 illustrates a precise mode which reads material frequencies at 100 ms.

Data measured as above is displayed on the LCD (15) equipped in the PC or diagnostic device.

Upon being transmitted to the PC from the diagnostic device equipped with the material for the detection of biological electro-magnetic signals as above, the data is transmitted according to a specific data transmission protocol by the radio communication module (19a), the USB port (19b) and the RS-232C (19c) of the PC or diagnostic device. The transmission protocol is divided into the prescan mode in FIG. 8 and the precise mode in FIG. 9. In the case of the prescan mode, measurement data is transmitted continuously until a break signal is inputted, that is, the user presses a stop button or the PC sends a stop command. On the contrary, the precise mode sends all data of the multi-channel material ten (10) times and then stands by until the user pushes a measurement button.

In addition, an audio signal is outputted through the buzzer (16b) so that the biological electro-magnetic signal inputted from the material can be heard. As different sounds are generated according to colors displayed on the LCD (15), normal condition, inflammation and cancer can be judged by sounds.

Figure 4:
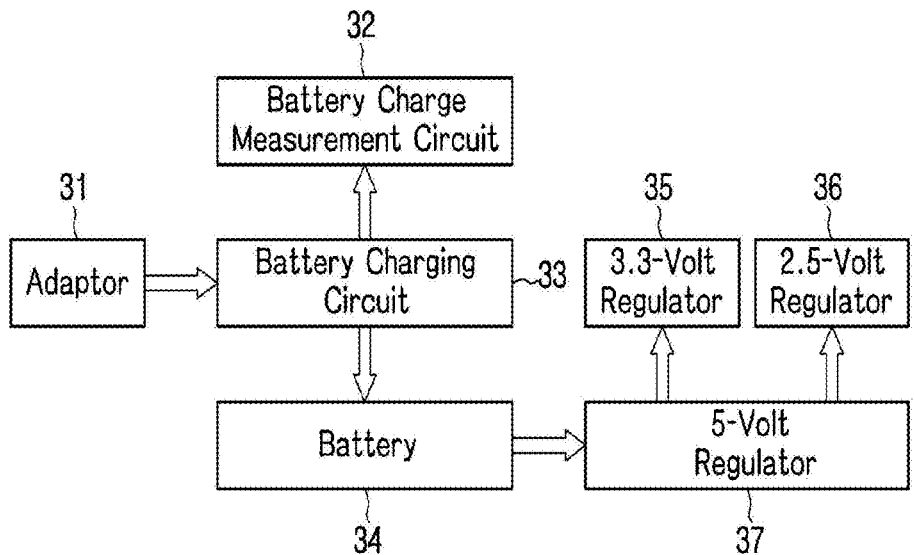
FIG. 4 is a block diagram illustrating a power circuit of the diagnostic device of the invention.

The power circuit (3) of FIG. 1 is also shown in FIG. 4, and includes the adaptor (31), the battery charge measurement circuit (32), the battery charging circuit (33), the battery (34), the 3.3 volt regulator (35), the 2.5 volt regulator (36), the 5 volt regulator (37) and the like. 3.3 volt and 2.5 volt are supplied to the digital conversion circuit 1 and 5 volt is supplied to the analog circuit (2). The battery 34 is implemented with a Nickel Metal Hybrid (Ni-MH) battery, which has a capacitance of about 1200 mA/H and thus can power the diagnostic device of the invention at a current of 55 OmA for about 2 hours.

The diagnostic device of the invention is a medical device and thus does not directly use a commercial or common voltage to ensure safety for a subject (living organism). Even though the adaptor (31) is used, the diagnostic device is powered from the battery (34). To check the residual capacity and charged capacity of the battery (34), the voltage of the battery (34) is feed back to the CPU (11) by the battery charge measurement circuit (32).

Biological electro-magnetic signals detected by the sensor probe (4) are analyzed by an algorithm stored in the analog circuit (2) and the digital conversion circuit (1), and then displayed on the screen.

Also the biological electro-magnetic signal inputted by the sensor probe (4) is displayed with irregular images by the algorithm set to the CPU program in the analog circuit (2), the digital conversion circuit (3) and CPU in the digital conversion circuit (3), it is diagnosed as cancer.

Alternatively, a frequency applied to the buzzer may be changed whenever a final result is changed so that an inspector or a subject may recognize the state of the diagnosed region by hearing.

After the biological electro-magnetic signal inputted into the sensor probe (4) is processed by the analog circuit (2), the digital conversion circuit 1 and so on, it can be transmitted to the PC via a wired/wireless communication module so that relevant data such as a diagnosed region, a diagnosis result and a clinical history can be classified as unique to the subject and stored in the database of the PC.

In an experimental example of the invention, the diagnostic device of the invention was used to diagnose cancer in mice whose subcutaneous tissue and abdominal cavity were implemented with cancer cells.

As a result of measuring biological electro-magnetic signals of the subject mouse by the diagnostic device of the invention, "green" or "yellow" as in FIG. 10 or 11 indicates that the subject mouse has an excellent or good condition, "red" in a regular state as in FIG. 12 indicates that the subject mouse has an inflammation, and "red" and "yellow" in an irregular state as in FIG. 13 indicates that the subject mouse has cancer.

A total of 656 measurements were carried out for three weeks using this method, on mice including those whose subcutaneous tissue was transplanted with cancer cells. In the initial seven (7) days after the transplantation, correct were 166 out of 190 measurements (87.4%), in which normal, healthy mice were not diagnosed with cancer. The total results were 629 hits out of 656 measurements (95.9%) in the experiment period, in which normal, healthy mice were not diagnosed with cancer. It can be appreciated that the diagnostic device of the invention has excellent sensitivity to biological electro-magnetic signals caused by cancer.

In another experimental example of the invention, the diagnostic device of the invention was used to diagnose cancer in the mice whose abdominal cavity was transplanted with leukemia cells. As a result, 84.7% were diagnosed with cancer in a control group, and the remaining 15.3% were diagnosed with inflammation instead of cancer. In the mice whose abdominal cavity was transplanted with leukemia cells, 93.1% were diagnosed with cancer. In view of the fact that cancer will not be induced in the control group but the group transplanted with cancer has a high probability of cancer, it can be appreciated that the diagnostic device of the invention has excellent sensitivity to biological electro-magnetic signals caused by cancer.

Accordingly, the invention provides a material for the detection of biological electro-magnetic signals using a epidermis and a diagnostic device using the same.

(Mode for Invention)

Examples of the invention will now be described in detail.

However, it should be appreciated that the following examples are to illustrate the invention but do not restrict the scope of the invention.

Example 1

Material for the Detection of Biological Electro-Magnetic Signals Made of Carp Epidermis (Scale)

A dead body of a carp was immersed in tap water at 30° C. for seven (7) days. Scales were separated from the dead body by physical force. Any tissues other than scales peeled off the body were removed from the scales, foreign materials were removed, and moisture was removed from the surface.

The separated scales were spread flat, applied under a pressure of 1 kg/cm$^2$, dried at room temperature for forty-eight (48) hours in a condition that they can maintain flatness, and then dried at room temperature (25° C.) for 48 hours without pressure so that moisture can be removed completely.

Figure 14:
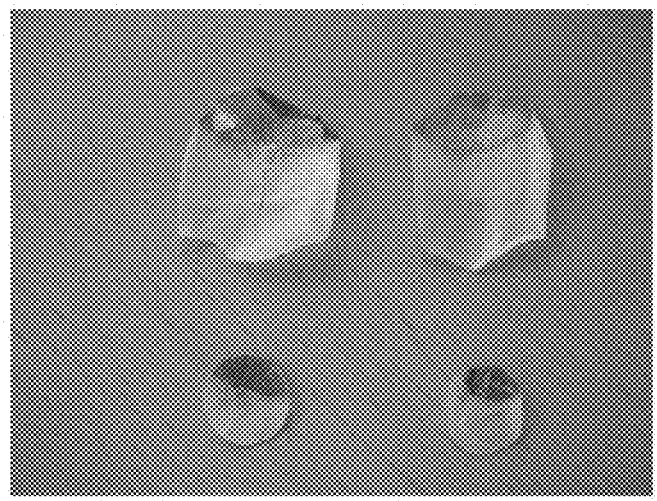
FIG. 14 is a picture illustrating materials detective to biological electro-magnetic signals produced from carp scales.

Pigment particulates contained in the scale include black melanin, red carotenoid, white guanine and so on. The scales which were completely dried have guanine and carotenoid in some regions (about 75% of the total area) and opaque, black melanin pigments in other regions (about 25% of the total area) (see FIG. 14). The scales were cut into circles having a diameter of about 15 mm, such that the black melanin region occupies at least 30% of the total area. The cut scales were measured for capacitance and conductivity by a capacitance meter (4263B LCR Meter, Agilent Technologies Ltd., USA) and a digital conductivity meter (Centurion NDT Inc, USA). Of the measured scales, those satisfying a capacitance range from 0.1 pF to 100 pF (6.5 pF in actual measurement) and a conductivity range from 0.01 nS to 20 nS (0.85 pF in actual measurement) were selected to obtain detective materials.

Example 2

Material for the Detection of Biological Electro-Magnetic Signals Made of Crucian Carp Epidermis (Scale)

Material for the detection of biological electro-magnetic signals was produced in the same fashion as in Example 1 except that a dead body of a crucial carp was used.

Example 3

Material for the Detection of Biological Electro-Magnetic Signals Made of Salmon Epidermis (Scale)

Material for the detection of biological electro-magnetic signals was produced in the same fashion as in Example 1 except that a dead body of a salmon was used.

Example 4

Material for the Detection of Biological Electro-Magnetic Signals Made of Trout Epidermis (Scale)

Material for the detection of biological electro-magnetic signals was produced in the same fashion as in Example 1 except that a dead body of a trout was used.

Example 5

Material for the Detection of Biological Electro-Magnetic Signals Made of Turtle Epidermis (Scale)

A dead body of a turtle was immersed in tap water at 33° C. for twenty-eight (28) days. Epidermis were separated from the dead body by physical force. Any tissues other than epidermis peeled off the body were removed from the epidermis, foreign materials were removed, and moisture was removed from the surface.

The separated epidermis were spread flat, applied under a pressure of 10 kg/cm², dried at room temperature for forty-eight (48) hours in a condition that they can maintain flatness, and then dried at room temperature (25° C.) for 48 hours without pressure so that moisture can be removed completely.

Figure 15:
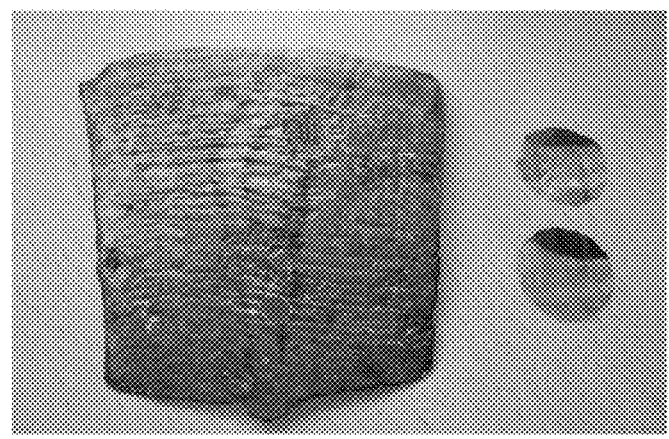
FIG. 15 is a picture illustrating materials detective to biological electro-magnetic signals produced from turtle epidermis.

The epidermis, which were completely dried (see FIG. 15), were cut into circles having a diameter of about 15 mm. The cut epidermis were measured for capacitance and conductivity by a capacitance meter and a digital conductivity meter. Of the measured epidermis, those satisfying a capacitance range from 0.1 pF to 100 pF and a conductivity range from 0.01 nS to 20 nS were selected to obtain detective materials.

Example 6

Material for the Detection of Biological Electro-Magnetic Signals Made of Snapping Turtle Epidermis Scale)

Material for the detection of biological electro-magnetic signals was produced in the same fashion as in Example 5 except that a dead body of a snapping turtle was used.

Example 7

Material for the Detection of Biological Electro-Magnetic Signals Made of Crocodile Epidermis (Scale)

Crocodile epidermis separated from the dead body were spread flat, applied under a pressure of 10 kg/cm², dried at room temperature for forty-eight (48) hours in a condition that they can maintain flatness, and then dried at room temperature (25° C.) for 48 hours without pressure so that moisture can be removed completely.

The epidermis, which were completely dried (see FIG. 15), were cut into circles having a diameter of about 15 mm. The cut epidermis were measured for capacitance and conductivity by a capacitance meter and a digital conductivity meter. Of the measured epidermis, those satisfying a capacitance range from 0.1 pF to 100 pF and a conductivity range from 0.01 nS to 20 nS were selected to obtain detective materials.

Example 8

Material for the Detection of Biological Electro-Magnetic Signals Made of Snake Epidermis (Scale)

Material for the detection of biological electro-magnetic signals was produced in the same fashion as in Example 5 except that a dead body of a snake was immersed in tap water at 33° C. for seven (7) days, epidermis were divided uniformly at a 30 cm length, foreign materials were removed, and moisture was removed from the surface.

Example 9

Material for the Detection of Biological Electro-Magnetic Signals Made of Beetle Epidermis (Cuticle)

Cuticle were separated from a dead body of a beetle by physical force. Any tissues other than cuticle peeled off the body were removed from the cuticle, foreign materials were removed from the cuticle, which were then cut into circles having a diameter of 5 mm, and then moisture was removed from the surface.

The separated cuticle were spread flat, applied under a pressure of 5 kg/cm², dried at room temperature for twenty-four (24) hours in a condition that they can maintain flatness, and then dried at room temperature (25° C.) for 48 hours without pressure so that moisture can be removed completely.

The cuticle, which were completely dried, were measured for capacitance and conductivity by a capacitance meter and a digital conductivity meter. Of the measured cuticle, those satisfying a capacitance range from 0.1 pF to 100 pF and a conductivity range from 0.01 nS to 20 nS were selected to obtain detective materials.

Example 10

Material for the Detection of Biological Electro-Magnetic Signals Made of Grasshopper Epidermis (Cuticle)

Material for the detection of biological electro-magnetic signals was produced in the same fashion as in Example 9 except that a dead body of a grasshopper was used.

Example 11

Material for the Detection of Biological Electro-Magnetic Signals Made of Gold Bug Epidermis (Cuticle)

Material for the detection of biological electro-magnetic signals was produced in the same fashion as in Example 9 except that a dead body of a gold bug was used.

Example 12

Material for the Detection of Biological Electro-Magnetic Signals Made of Ladybug Epidermis (Cuticle)

Material for the detection of biological electro-magnetic signals was produced in the same fashion as in Example 9 except that a dead body of a ladybug was used.

Example 13

Material for the Detection of Biological Electro-Magnetic Signals Made of Crab Epidermis (Shell)

shell were separated from a dead body of a crab by physical force. If any tissues or internal organs other than shell were peeled off the body, the shell were immersed in tap water at 33° C. for four (4) days to remove foreign materials such as tissues and internal organs from the shell. The shell were cut into circles having a diameter of 15 mm, foreign materials were removed, and moisture was removed from the surface.

The separated shell were spread flat, applied under a pressure of 1 kg/cm$^2$, dried at room temperature for forty-eight (48) hours in a condition that they can maintain flatness, and then dried at room temperature (25° C.) for 48 hours without pressure so that moisture can be removed completely.

The shell, which were completely dried, were measured for capacitance and conductivity by a capacitance meter and a digital conductivity meter. Of the measured shell, those satisfying a capacitance range from 0.1 pF to 100 pF and a conductivity range from 0.01 nS to 20 nS were selected to obtain detective materials.

Example 14

Material for the Detection of Biological Electro-Magnetic Signals Made of Shrimp Epidermis (Shell)

Material for the detection of biological electro-magnetic signals was produced in the same fashion as in Example 13 except that a dead body of a shrimp was used.

Example 15

Material for the Detection of Biological Electro-Magnetic Signals Made of Lobster Epidermis (Shell)

Material for the detection of biological electro-magnetic signals was produced in the same fashion as in Example 13 except that a dead body of a lobster was used.

Example 16

Diagnostic Device Manufactured Using Material for The Detection of Biological Electro-Magnetic Signals Ten (10) materials for the detection of biological electro-magnetic signals produced in Example 1 were overlapped one on another and fixed between electrodes of the sensor probe shown in FIG. 1 to manufacture a diagnostic device for detecting biological electro-magnetic signals according to the block diagrams shown in FIGS. 1 to 5.

Experimental Example 1

Test of Material for the Detection of Biological Electro-magnetic Signals about Cancer Diagnosis The diagnosis device manufactured in Example 16 was used to determine the ability of the detective material to detect biological electro-magnetic signals by cancer diagnosis test.

Mice to be tested were specific pathogen free BALB/C nude mice (Athymic BALB/C Nude Mouse), which were 8 weeks old female mice removed of thymus (available from Central Lab. Animals Inc., Korea). Test mice were grouped into groups in the order of weight, including one (1) control group and five (5) hypodermic implantation groups, in which each group is composed of 10 mice. For recognition, identification labels on breeding boxes and ear punches were used. However, only group identification was allowed during test period, and group-based carcinoma was not informed to a worker who performed experiments.

Test groups are as reported in Table 2 below:

TABLE 2

| Group No. | Sex | Animal per Group | Animal No. | Amount of Transplanted Cancer (cells/head) | Origin of Cancer |
| --- | --- | --- | --- | --- | --- |
| G1 | F | 10 | 1 to 10 | — | Control group |
| G2 | F | 10 | 11 to 20 | $0.3 \times 10^7$ | Lung cancer |
| G3 | F | 10 | 21 to 30 | $0.3 \times 10^7$ | Colon cancer |
| G4 | F | 10 | 31 to 40 | $0.3 \times 10^7$ | Melanoma |
| G5 | F | 10 | 41 to 50 | $0.3 \times 10^7$ | Prostate cancer |
| G6 | F | 10 | 51 to 60 | $0.3 \times 10^7$ | Breast cancer |

* Note
G1: Group where cancer cells are not transplanted
G2 to G6: Groups where cancer cells are transplanted Mice were bred at a temperature of 23±3° C. and a relative moisture of 55±15%, and allowed to intake water and feed freely.

Used cancer cell lines were originated from the human such as lug cancer (A549), colon cancer (HCT15), melanoma (LOX-IMVI), prostate cancer (PC-3) and breast cancer (MDA-MB-231), obtained from Korea Research Institute of Bioscience and Biotechnology.

The respective cancer cell lines were suspended as soon as possible in a water bath (37° C.), mixed uniformly into RPMI1640 culture media (SigmaAldrich, USA) containing 10% FBS (fetal bovine serum, Fetal Bovine Serum, SigmaAldrich, USA), and centrifuged at 1200 rpm for 10 minutes. After the centrifuge, supernatant was discarded, and the separated cell were mixed uniformly into RPMI1640 culture media of 5 ml, placed into a cell culture flask, and then cultured in incubator in 5% $CO_2$ and at 37° C.

The cultured cancer cells were suspended in a saline solution to $1\times10^7$ cells/ml. The saline solution containing the cancer cells was transplanted by 0.3 ml to the respective mice, under the skin. 0.3 ml saline solution was injected into a control group.

By using the diagnostic device manufactured in Example 16, the carcinogenesis aspect of animals was measured randomly according to the groups from the first day of cancer cell transplantation. The diagnosing ability of the diagnostic device using the material of the invention was estimated by comparison with histopathological analysis.

According to measurement results, at a reference frequency of 50,400 Hz of the diagnostic device manufactured in Example 16, those mice showing a measurement frequency of 50,400 Hz to 48,380 Hz were very healthy (green), and those mice showing a measurement frequency ranging from 48,370 Hz to 46,790 Hz were relatively healthy (yellow). When "yellow" and "red" were displayed irregularly, it is judged to be cancer. In the respective judgment, reference points were established by results obtained by experiences of the inventors and preliminary experiments, and previously inputted so that the CPU of the diagnostic device can make judgment according to frequency values of corresponding ranges. In particular, the differences of measurement frequencies in respective measurements are maintained uniform in the case of normal condition. In the case of inflammation, the measurement frequencies are lower than those of the normal condition but maintain uniform frequency differences. However, in the case of cancer, the measurement frequencies showed a large deviation, in particular, maintained a similar or lower level than the case of inflammation, suddenly rose to the level of normal frequency range, and then dropped to the frequency range of inflammation. In this way, the measurement frequencies show large differences at respective measurements.

When measurements were carried out seven (7) days after the transplantation of the cancer cells, a tumor could not be recognized by eye but the measurement results are reported in Table 3 below. Hit ratios were produced by dividing the number of normal conditions with the total number of measurements in the case of control group, and by dividing the number of cancer diagnoses with the total number of measurements in the case of hypodermic implantation group. The hit ratio on the control group was 93.3% (28/30), the hit ratio on the hypodermic implantation group was 86.3% (138/160), and the overall hit ratio was 87.4% (166/190). The overall results including a period where tumors could be observed by eye are reported in Table 4 below, in which the hit ratio on the control group was 96.5% (111/115), the hit ratio on the hypodermic implantation group was 95.7% (518/541), and the overall hit ratio was 95.9% (629/656).

TABLE 3

|  | G1 | G2 | G3 | G4 | G5 | G6 | Total |
|---|---|---|---|---|---|---|---|
| Total Measurement | 30 | 35 | 35 | 30 | 30 | 30 | 190 |
| Normal (N) | 28 | 0 | 1 | 1 | 0 | 0 |  |
| Inflammation (I) | 2 | 7 | 2 | 3 | 3 | 5 |  |
| Cancer (C) | 0 | 28 | 32 | 26 | 27 | 25 |  |

TABLE 4

|  | G1 | G2 | G3 | G4 | G5 | G6 | Total |
|---|---|---|---|---|---|---|---|
| Total Measurement | 115 | 115 | 115 | 101 | 105 | 105 | 656 |
| Normal (N) | 111 | 0 | 1 | 1 | 0 | 0 |  |
| Inflammation (I) | 4 | 7 | 2 | 3 | 3 | 6 |  |
| Cancer (C) | 0 | 108 | 112 | 97 | 102 | 99 |  |

In view of the results, the measuring test was carried out a total of 656 times for three (3) weeks by the diagnostic device, which was manufactured using the material for the detection of biological electro-magnetic signals. The measurements by the diagnostic device manufactured using the material for the detection of biological electro-magnetic signals showed 166 hits out of a total of 190 measurements (87.4%) up to 7 days after the implantation of the cancer cells, but never diagnosed with cancer in a normal, healthy mouse. In addition, the overall results showed 629 hits out of the total 656 measurements (95.9%), in which no normal mice were wrongly diagnosed with cancer.

Hypodermic tumors were extracted from all the mice, and all of them were tested positive for cancer tissues as a result of histopathological examination.

When common symptoms were observed, no special symptoms were found from the animals except for those symptoms specific to cancer growth. In the group where melanoma was transplanted, mice died by one, respectively, on $15^{th}$, $18^{th}$ and $21^{st}$ days.

Experimental Example 2

Test of Material for the Detection of Biological Electro-magnetic Signals about Leukemia Diagnosis The ability of the diagnostic device manufactured in Example 16 to diagnose cancer was tested according to the same fashion as Experimental Example 1 except that leukemia (K562) obtained from Korea Research Institute of Bioscience and Biotechnology was transplanted into the abdominal cavity.

Test groups are as reported in Table 5 below:

TABLE 5

| Group No. | Sex | Animal per Group | Animal No. | Amount of Transplanted Cancer (cells/head) | Origin of Cancer |
|---|---|---|---|---|---|
| G7 | F | 20 | 1 to 20 | — | Control group |
| G8 | F | 20 | 21 to 40 | $0.3 \times 10^7$ | Leukemia |

G7: Group where cancer cells are not transplanted
G8: Group where cancer cells are transplanted Measurement results are as reported in Table 6 below:

TABLE 6

|  | G7 | G8 | Total |
|---|---|---|---|
| Total Measurement | 150 | 145 | 295 |
| Normal (N) | 127 | 0 | |
| Inflammation (I) | 23 | 10 | |
| Cancer (C) | 0 | 135 | |

After transplantation of cancer cells, 84.7% (127/150) of the control group was diagnosed normal, and remaining 15.3% (23/150) was diagnosed with inflammation but not with cancer. In the case of the group transplanted with leukemia, 93.1% (135/145) was diagnosed with cancer. However, hit ratios could not be calculated since carcinogenesis was not proved histopathologically.

In the case of mice with leukemia transplanted into the abdominal cavity, a plurality of cases were observed in one of the mice used in the experiment at the time point where the experiment ended. Thus, if the experiment period was prolonged, it could be possible to identify carcinogenesis.

INDUSTRIAL APPLICABILITY

As described hereinbefore, the detective material of the invention has an effect of detecting biological electro-magnetic signals. Accordingly, the material for the detection of biological electro-magnetic signals of the invention can be used for manufacturing a diagnostic device for detecting biological electro-magnetic signals non-invasively as well as effectively used in diagnosis in cases where biological electro-magnetic signals are changed by cancer, inflammations due to immunodeficiency and so on.

The invention claimed is:

1. A method of manufacturing a material for the detection of biological electro-magnetic signals, comprising steps of:
   a) drying an epidermis separated from a living organism;
   b) measuring a capacitance on the dried epidermis to select the epidermis, wherein the epidermis separated from the living organism is selected from a group consisting of a scale of a fish, a scale or horny scale layer of a reptile, a modified skin of a bird, a cuticle of an insect, a cuticle of a mollusk, a cuticle of a shellfish, a feather, and a shell or horny scale layer of a crustacean.

2. The method according to claim 1, further comprising: immersing the epidermis into water.

3. The method according to claim 1, wherein the step a) comprises drying the epidermis for 1 to 48 hours under a pressure of 0.5 kg/cm$_2$ to 10 kg/cm$^2$ and then drying the epidermis for 1 to 96 hours without pressure.

4. The method according to claim 1, wherein the step b) comprises of selecting the dried capacitance of the epidermis that is in a range from 0.1 pF to 100 pF.

5. The method according to claim 1, further comprising: measuring a conductivity of the epidermis to select the epidermis.

6. The method according to claim 5, wherein the conductivity of the epidermis is in a range from 0.01 nS to 20 nS.

7. The method according to claim 1, further comprising: measuring a permittivity of the epidermis to select the epidermis.

8. The method according to claim 7, wherein the permittivity is in a range from 0.1 F/m to 50 F/m.

9. The method according to claim 1, wherein the epidermis has a thickness in a range from 0.01 mm to 10 mm and a diameter in a range from 0.1 mm to 100 mm by the step b).

10. The method according to claim 1, wherein the epidermis separated from the living organism is a scale of a fish.

11. The method according to claim 10, wherein the fish is selected from a group consisting of carp, a crucian carp, salmon and trout.

12. The method according to claim 1, wherein the epidermis separated from the living organism is a scale or skin of a reptile.

13. The method according to claim 12, wherein the reptile is selected from a group consisting of a turtle, a snapping turtle, a crocodile and a snake.

14. The method according to claim 1, wherein the epidermis separated from the living organism is a cuticle of an insect.

15. The method according to claim 14, wherein the insect is selected from a group consisting of a beetle, a grasshopper, a gold bug and a ladybug.

16. The method according to claim 1, wherein the epidermis separated from the living organism is a shell of a crustacea.

17. The method according to claim 16, wherein the crustacea is selected from crab, shrimp and crayfish.

18. The method according to claim 1, wherein the epidermis is a scale transformed from a dermis, or a retrogressed or cornified scale.

* * * * *